US006764460B2

(12) United States Patent
Dolecek et al.

(10) Patent No.: US 6,764,460 B2
(45) Date of Patent: Jul. 20, 2004

(54) EXTRACORPOREAL BLOOD PROCESSING SYSTEM

(75) Inventors: Victor D. Dolecek, Englewood, CO (US); John J. Kappus, Denver, CO (US); Mark Joseph Brierton, Morrison, CO (US)

(73) Assignee: Gambro Inc., Lakewood, CO (US)

( * ) Notice: Subject to any disclaimer, the term of this patent is extended or adjusted under 35 U.S.C. 154(b) by 64 days.

(21) Appl. No.: 09/911,955

(22) Filed: Jul. 24, 2001

(65) Prior Publication Data

US 2002/0028155 A1 Mar. 7, 2002

Related U.S. Application Data

(60) Division of application No. 09/150,543, filed on Sep. 9, 1998, now Pat. No. 6,280,406, which is a continuation-in-part of application No. 08/949,041, filed on Oct. 10, 1997, now Pat. No. 6,409,696.
(60) Provisional application No. 60/058,587, filed on Sep. 12, 1997.

(51) Int. Cl.[7] .................. A61M 37/00; A61M 1/00; C02F 1/44; C02F 1/00; C02F 1/38
(52) U.S. Cl. ................ 604/6.01; 604/4.01; 604/28; 210/645; 210/741; 210/782
(58) Field of Search .................. 604/4.01, 5.01, 604/6.01–6.06, 6.1, 6.11, 6.16, 19, 27–31, 34, 65–67, 153; 422/44; 210/787–89, 645, 739, 741, 767, 781, 722, 85, 87, 90, 252, 258–60, 257.1–257.2, 321.6, 321.72, 359, 360.1; 128/DIG. 3, 905, 920, 923; 494/1, 10, 37, 60, 61; 73/1.01, 1.57, 1.59, 1.87, 37, 861, 195, 198–99, 861.42–861.47, 861.69, 232, 262–271

(56) References Cited

U.S. PATENT DOCUMENTS

| 2,535,998 A | 12/1950 | Bierman ....................... 73/309 |
| 3,713,341 A | 1/1973 | Madsen et al. ................ 73/406 |
| 3,738,356 A | 6/1973 | Workman ............... 128/2.05 D |

(List continued on next page.)

FOREIGN PATENT DOCUMENTS

| DE | 28 23 670 A1 | 6/1979 |
| EP | 28 23 670 A1 | 12/1979 |
| EP | 0 685 721 A2 | 6/1995 |
| EP | 0685721 | 3/1997 |
| GB | 2 208 714 A | 4/1989 |
| WO | WO 96/05494 | 2/1996 |
| WO | WO 96/40322 | * 12/1996 |

*Primary Examiner*—Patricia Bianco
(74) *Attorney, Agent, or Firm*—Edna M. O'Connor; Laura M. Butterfield

(57) ABSTRACT

An extracorporeal blood processing system including a disposable assembly that has integral fluid passageways. A blood removal conduit and a blood return conduit are interconnected with the integral fluid passageways. A diaphragm is mounted in the disposable assembly and is removably attachable to a sensor via a number of connection devices. In one embodiment, the sensor may include a transducer that is capable of measuring the force exerted on the diaphragm. The corresponding force may be correlated to a pressure of fluid in either the blood removal conduit and/or the blood return conduit.

21 Claims, 10 Drawing Sheets

U.S. PATENT DOCUMENTS

| | | | |
|---|---|---|---|
| 3,908,653 A | 9/1975 | Keltering | 128/214 R |
| 4,077,882 A | 3/1978 | Gangemi | |
| 4,109,535 A | 8/1978 | Reed et al. | |
| 4,204,538 A | 5/1980 | Cannon | |
| 4,226,124 A | 10/1980 | Kersten | |
| 4,227,420 A | 10/1980 | Lamadrid | 73/756 |
| 4,263,808 A | 4/1981 | Bellotti et al. | |
| 4,347,744 A | 9/1982 | Buchanan | |
| 4,412,916 A | 11/1983 | Kell | |
| 4,530,759 A | 7/1985 | Schäl | |
| 4,545,389 A | 10/1985 | Schaberg et al. | |
| 4,625,757 A | 12/1986 | Dykstra et al. | 137/504 |
| 4,758,228 A | 7/1988 | Williams | 604/153 |
| 4,775,470 A | 10/1988 | Zook | |
| 4,790,937 A | 12/1988 | Eilers | |
| 4,798,090 A | 1/1989 | Heath et al. | |
| 4,798,580 A | 1/1989 | DeMeo et al. | 604/30 |
| 4,856,339 A | 8/1989 | Williams | 73/714 |
| 5,392,653 A * | 2/1995 | Zanger et al. | 73/756 |
| 5,554,115 A | 9/1996 | Thomas et al. | 604/65 |
| 5,591,344 A | 1/1997 | Kenley et al. | 210/636 |
| 5,693,039 A | 12/1997 | Stewart et al. | |
| 5,720,741 A | 2/1998 | Stewart et al. | |
| 5,795,317 A * | 8/1998 | Brierton et al. | 604/5.01 |
| 6,280,406 B1 * | 8/2001 | Dolecek et al. | 604/4.01 |

* cited by examiner

EXTRACORPOREAL BLOOD PROCESSING SYSTEM

RELATED APPLICATIONS

This application is a divisional of U.S. application Ser. No. 09/150,543 filed Sep. 9, 1998, now U.S. Pat. No. 6,280,406, which is a continuation-in-part of U.S. patent application Ser. No. 08/949,041, filed Oct. 10, 1997, now U.S. Pat. No. 6,409,696 and also a non-provisional of U.S. Provisional Application No. 60/058,587 filed Sep. 12, 1997.

FIELD OF THE INVENTION

The present invention relates generally to an extracorporeal blood processing system and more particularly to a method and apparatus using a removably coupled force sensor capable of indicating pressure in a blood removal conduit and/or a blood return conduit.

BACKGROUND OF THE INVENTION

Extracorporeal blood processing systems remove blood from a patient's body, process the blood for some purpose and return it to the body. One type of extracorporeal blood processing is an apheresis procedure in which blood from a donor is directed to a blood component separation device (e.g., centrifuge). The blood is separated into various blood component types (e.g., red blood cells, white blood cells, platelets, plasma) for collection or therapeutic purposes while the remainder are returned to the donor. Apheresis procedures are often conducted at clinics with multiple donors being processed on a single apheresis machine in a single day. Another type of extracorporeal blood processing is an oxygenation procedure in which blood is removed from a patient, directed to a blood oxygenation device where the blood is oxygenated and returned to the patient. This blood procedure is useful in ensuring that freshly oxygenated blood is circulated to the patient during surgery when the heart and lungs are stopped. Other extracorporeal blood processing techniques, such as hemodialysis, blood salvage and blood washing are also well-known.

In extracorporeal systems, such as those mentioned above, positive and negative pressures must be accurately monitored as blood is removed from and returned to the patient. In addition, it is highly desirable for blood processing systems to use a disposable assembly for any portion of the system which contacts the blood. For such systems, the mechanism for monitoring pressure must be capable of connecting with and monitoring blood pressure in the disposable assembly.

In previous blood processing systems, pressure has been measured using a pressure sensor in communication with a blood conduit. In one such embodiment, a diaphragm is incorporated into the blood conduit, and blood, in the conduit, contacts one surface of the diaphragm while a captive air space is in contact with a second surface of the diaphragm. A pressure sensor communicates with the captive air space. In addition, the pressure sensor measures the pressure changes in the captive air space as the diaphragm flexes in response to the pressure changes in the blood conduit. Such a system is not entirely satisfactory. If an air leak develops in the captive air space, the sensor is not capable of accurately measuring pressure in the blood conduit. In another blood processing system, pressure in a blood conduit has been measured by a force sensor placed around the blood conduit. To determine the pressure of the blood within the conduit, the force sensor measures the expansion of the blood conduit. These pressure monitoring systems have been known to produce less than accurate pressure measurements, especially for negative pressures.

A need, therefore, exists for a blood processing system having a sensor that is capable of measuring positive and negative pressure of a fluid flowing through a conduit. Such a system should be suitable for use in measuring pressures within a disposable assembly, and the sensor should be capable of being removably coupled with the disposable assembly. Moreover, such a system should avoid the durability problems associated with pressure measuring systems using captive air spaces.

SUMMARY OF THE INVENTION

The present invention generally relates to extracorporeal blood processing systems. Each of the various aspects of the present invention may be incorporated into, for example, an apheresis system (e.g., where blood components are separated) and other extracorporeal blood processing applications which are within the scope of the present invention.

An extracorporeal blood processing system which embodies one or more aspects of the present invention generally includes a blood removal conduit for transporting blood from a donor/patient and a blood return conduit for transferring blood to the donor/patient. A portion of the blood removal conduit and a portion of the blood return conduit are in fluid communication. A disposable assembly is provided that has a plurality of integral passageways used to transport blood. Each of the passageways is partially defined by either the blood removal conduit or the blood return conduit. In one embodiment, the disposable assembly comprises a molded cassette member that has a series of integral passageways which partially define the blood removal conduit and the blood return conduit.

In another aspect of the present invention, a pressure sensing station is connected in direct fluid communication with either a portion of the blood removal conduit or a portion of the blood return conduit. The pressure sensing station includes a diaphragm having a first surface in fluid communication with either the blood removal or blood return conduit. A second surface of the diaphragm is removably attached to a sensor. The diaphragm may comprise a flexible elastomeric material.

In one aspect of this embodiment, the sensor includes a pressure measuring mechanism, such as a strain gauge. Through the pressure measuring mechanism, the force exerted on the first surface of the diaphragm can be measured. The resultant force exerted on the diaphragm corresponds to the pressure of the blood in the corresponding blood conduit. In yet another aspect of this embodiment, the sensor may be a piezoelectric distance sensor for measuring the distance the diaphragm deflects and converting this distance into a pressure in the blood conduit.

In yet another aspect of this embodiment, a ferromagnetic material is attached to the second surface of the diaphragm, and a magnet is attached to the sensor. The magnet is capable of being directly coupled to the ferromagnetic material on the second surface of the diaphragm. As such, this coupling of the ferromagnetic material and the magnet create a removable attachment of the diaphragm and the sensor. In an alternative aspect, the magnet may be attached to the diaphragm and the ferromagnetic material may be attached to the sensor.

In a further embodiment of the present invention, the extracorporeal blood processing system can include a disposable assembly as broadly discussed above. In addition, the extracorporeal blood processing system includes a sensor which measures a quantity corresponding to positive and negative fluid pressures and which can be removably attached to the second surface of the diaphragm of the disposable assembly. The sensor may be removably attached to the second surface of the diaphragm.

In one aspect of this embodiment, a probe having a vacuum chamber is provided for interfacing with the second surface of the diaphragm. The probe is connected to the sensor, and when a vacuum is created in the vacuum chamber the probe is coupled to the second surface of the diaphragm.

A means for detecting a state of coupling between the vacuum chamber and the second surface of the diaphragm, such as a means for monitoring air flow, may also be provided. When air flow is detected, the probe is not connected to the second surface of the diaphragm and vice versa.

In another aspect of this embodiment, the diaphragm includes an elongated member attached to and extending from the second surface of the diaphragm. A means for attaching the second surface to a sensor is provided. The means for attaching includes a means for capturing the elongated member. In this aspect, the elongated member may have a shaped end. The means for attaching may further comprise a receiving structure having a complementary shaped opening corresponding to the shaped end of the elongated member. In addition, the means for attaching may also include a receiving element having an opening wherein the opening has a first size for accepting the shaped end and a second size, smaller that the first size, for capturing the shaped end.

In even another embodiment of the present invention, a method for measuring pressure in an extracorporeal blood processing system is provided. This method includes introducing blood from a donor/patient into a disposable assembly, wherein the disposable assembly has at least one blood conduit with a diaphragm member disposed within a wall of the conduit. The method further includes determining a pressure in the at least one blood conduit. The step of determining may include measuring a force of the blood on the diaphragm using a force sensor or displacement of the diaphragm. The measured force or displacement may then used to calculate a pressure of the blood in the blood conduit. The disposable assembly and extracorporeal blood processing system as broadly described above are useful in the method of the present invention.

DETAILED DESCRIPTION

Figure 1:
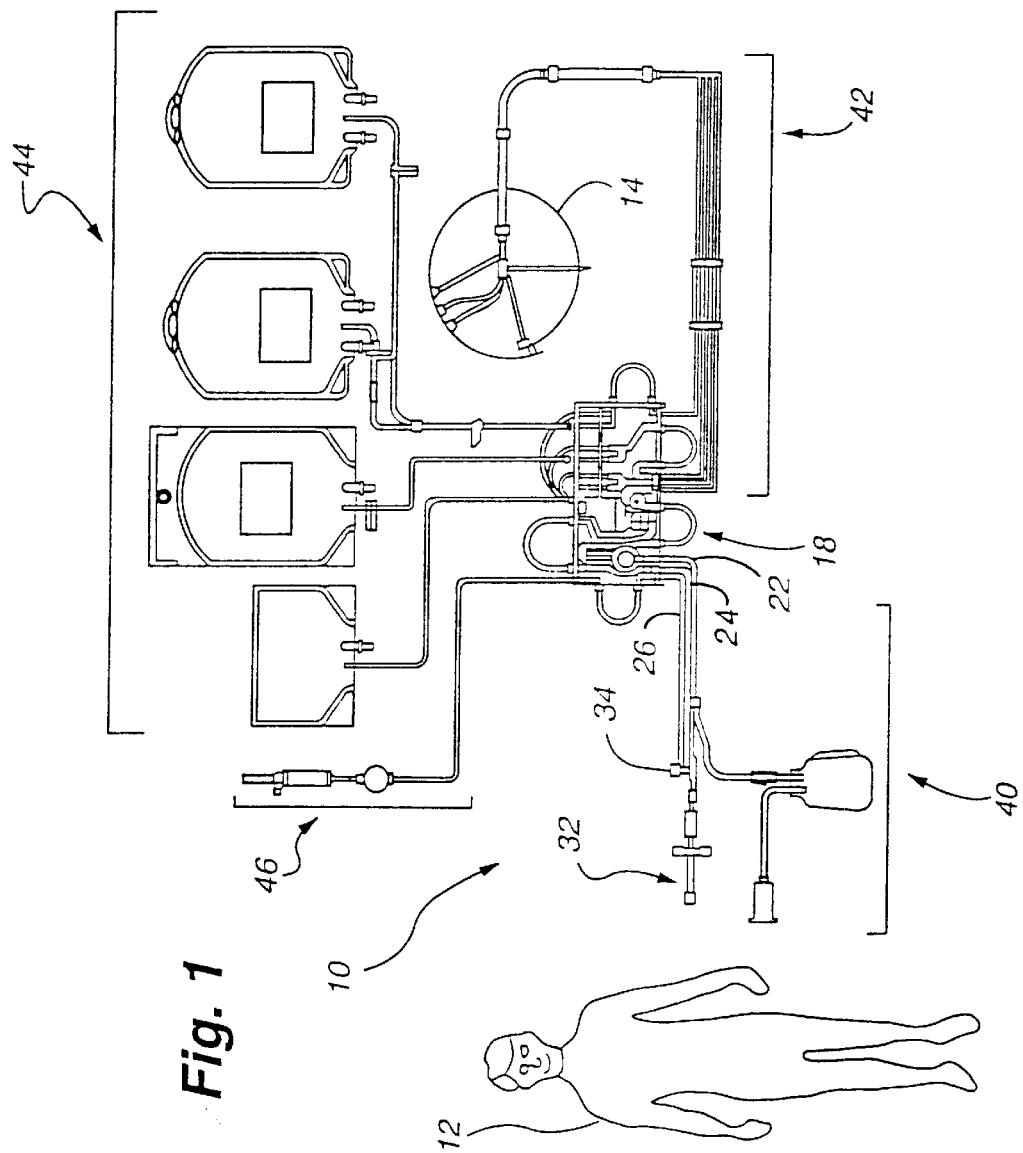
FIG. 1 is an illustration of one embodiment of an extracorporeal blood processing system.

Generally, the present invention relates to procedural and structural improvements in extracorporeal blood processing systems. As such, the improvements presented herein are applicable to all extracorporeal blood processing systems.

More specifically, the present invention relates to a disposable assembly for use in an extracorporeal blood processing system. As used herein, the term "extracorporeal blood processing system" refers to any method and apparatus for removing blood from a patient's body, performing therapeutic treatment or componentizing the blood, and reintroducing the blood or remaining portions thereof to the patient. Exemplary extracorporeal blood processing systems include an apheresis system which is generally described in U.S. Pat. No. 5,653,887; a perfusion system which is generally described in U.S. Pat. No. 4,663,125; a blood oxygenation system which is generally described in U.S. Pat. No. 5,489,413; and a hemodialysis system which is general described in U.S. Pat. Nos. 5,603,902 and 4,683,053, all of which are hereby incorporated by reference. It should be understood that the present invention is applicable to extracorporeal blood processing systems other than those generally described herein, such as blood salvage and blood washing systems.

By their nature, extracorporeal blood processing systems require the use of a disposable assembly to prevent the transmission of blood borne diseases. In the present invention, the assembly includes a blood removal conduit for transferring blood from a donor/patient and a blood return conduit for transferring blood to a donor/patient.

It should be recognized in this context that reference to a "donor" in the term "donor/patient" can refer to a person donating blood or blood components, such as during an apheresis procedure. In addition, the term "donor" can refer to a blood container, such as a bag, where previously drawn blood is processed. Such procedures are sometimes referred to as "bag-to-bag" procedures. Further, in this context, reference to a "blood removal conduit" refers to a conduit for removing blood from a blood container, and reference to a "blood return conduit" refers to a conduit for introducing blood to a blood container, even though the blood was not originally in that given container.

Typically, the blood removal conduit and blood return conduit include needles attached to tubing for conveying blood from or to the body. Extracorporeal blood processing systems can either be a single needle system in which blood is withdrawn from the body through the needle, directed to subsequent tubing and processed. Then, after processing, the blood is returned via blood return conduit tubing and is transferred back to the body through the same needle. Alternatively, an extracorporeal blood processing system can be a double needle system in which the blood removal conduit includes a first needle and tubing and the blood return conduit includes a second needle and tubing with the needles being inserted into separate locations in the body. In either embodiment, the blood removal conduit and the blood return conduit are in fluid communication so that as blood is removed and processed, the blood is then transported to the blood return conduit for return to the patient's body.

The assembly also includes a pressure sensor that is removably connected to a diaphragm which has a second surface that is in fluid communication with a portion of the blood removal conduit or the blood return conduit. The pressure sensor includes a load cell and a mechanism for removably attaching the sensor to a first surface of the diaphragm which is not in fluid communication with either the blood removal conduit or blood return conduit.

Typically, the load cell includes a spring-type element with a transducer attached thereto. The spring-type element comprises a material that is fairly resilient, such as aluminum, and is fabricated in the form of a parallel beam to prevent twisting or torsion of the element.

The transducer is affixed to one of the parallel beams of the load cell. When the diaphragm is attached to the sensor and the extracorporeal blood processing system is in use, the transducer can measure a force, displacement or other quantity exerted by fluid contacting the second surface of the diaphragm. More specifically, the transducer measurement is performed by detecting a stress or strain on the spring-type element or a deflection or flexing of the spring-type element that corresponds to positive and negative fluid pressure in the blood removal conduit or the blood return conduit.

A variety of mechanisms can be used to removably attach the first surface of the diaphragm to the sensor. For example, the mechanism for attaching the first surface of the diaphragm to the sensor can be a magnetic attachment mechanism. In addition, the mechanism for removably attaching the first surface of the diaphragm to the sensor can include a variety of other embodiments, including, without limitation, interlocking structures or any mechanical coupling that allows for easy attachment, e.g., threads, snaps and bolts.

The present invention will be described in relation to the accompanying drawings which assist in illustrating the pertinent features thereof. As noted above, the present invention may be used in conjunction with an apheresis system. In the apheresis process, the blood components may be provided for subsequent use by another or may undergo a therapeutic treatment and be returned to the donor/patient 12. As such, a disposable 10 for coupling to an apheresis system is illustrated in FIG. 1.

Figure 2:
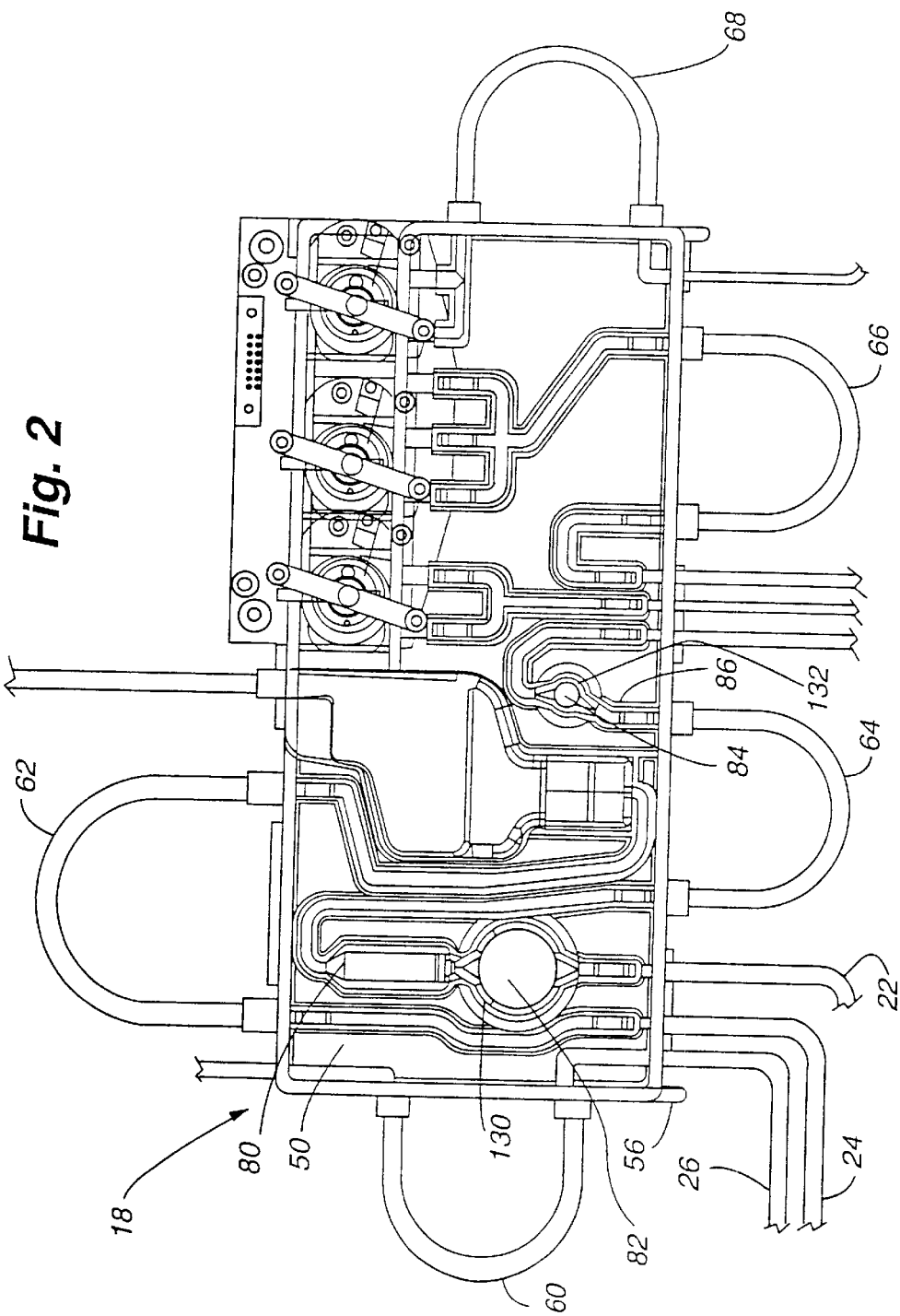
FIG. 2 illustrates an extracorporeal tubing circuit and cassette assembly for the system of FIG. 1.
Figure 3:
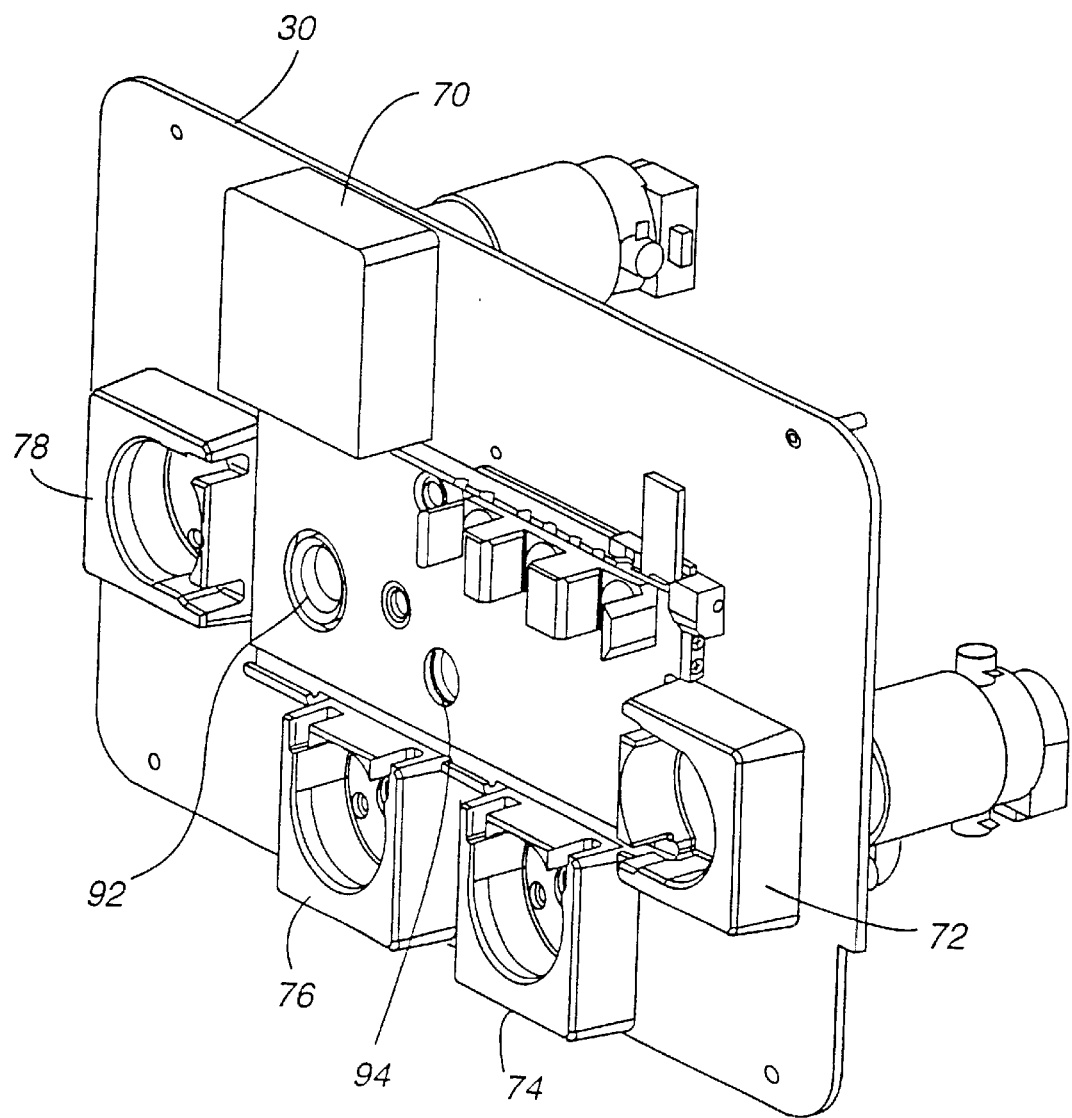
FIG. 3 is a perspective view of a cassette mounting plate for the cassette assembly of FIG. 2.

In the apheresis system in FIGS. 1–3, blood is withdrawn from the donor/patient 12 and directed through a cassette assembly 18 which interconnects extracorporeal tubing circuits 40, 42, 44, 46. From the cassette assembly 18, the blood is directed to blood processing device 14. In this embodiment, the blood processing device 14 includes a blood separation device that separates blood into various component types.

Typically, the blood removal/return tubing assembly 40 provides a single needle interface between the donor/patient 12 and the cassette assembly 18. Specifically, the blood removal/return tubing assembly 40 includes a needle subassembly 32 interconnected with blood removal tubing 22, blood return tubing 24 and blood additive tubing 26 via a common manifold 34.

The blood inlet/blood component tubing assembly 42 provides an interface between the cassette assembly 18 and the blood processing device 14. A blood additive tubing assembly 46 and vent bag assembly 44 are also interconnected with cassette assembly 18. As such, the extracorporeal tubing circuit 40, 42, 44 and 46 and the blood processing device 14 are interconnected to the cassette assembly 18 to combinatively produce a closed disposable for single use.

Figure 4:
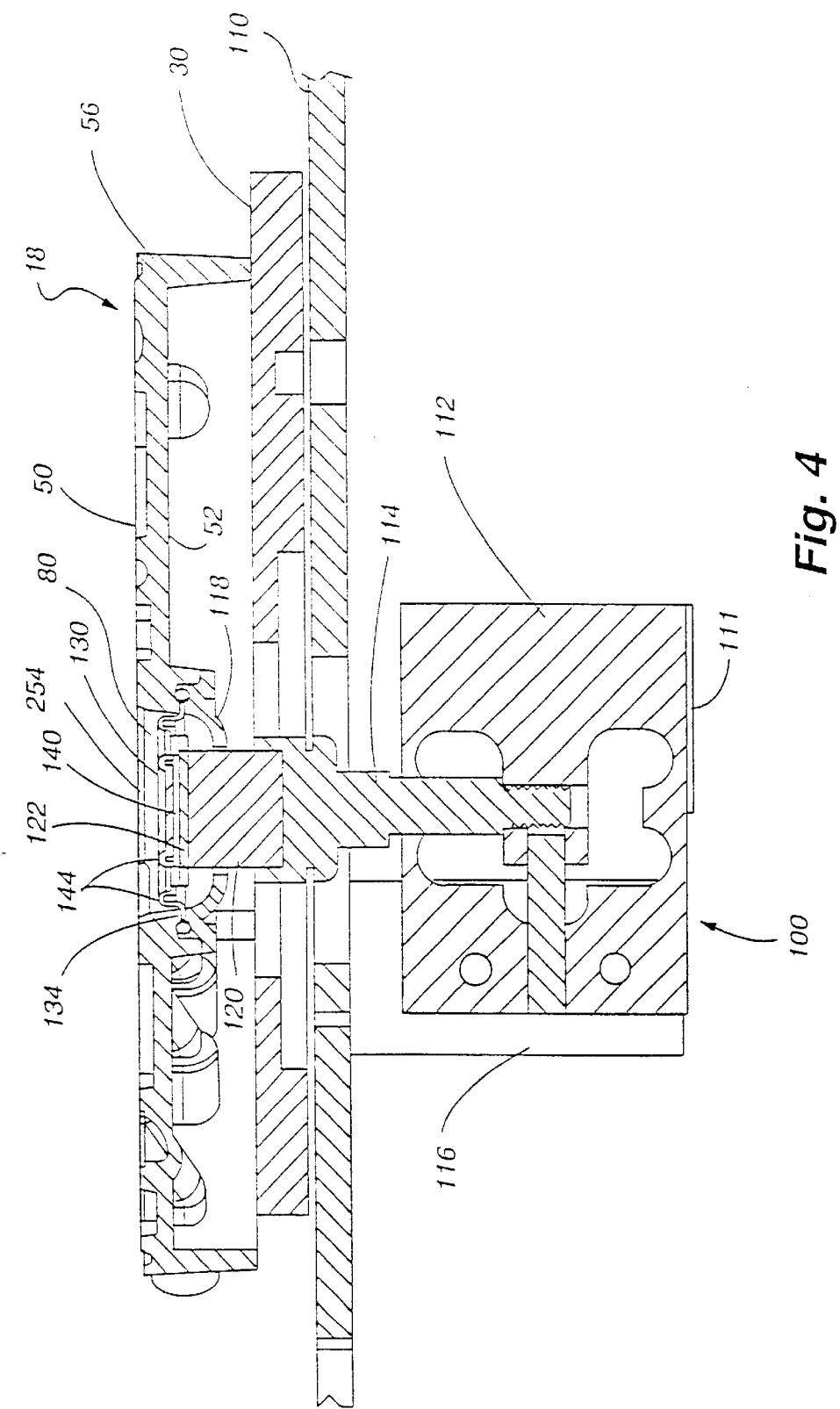
FIG. 4 is a cross-sectional view of a first embodiment of a pressure sensing module of the extracorporeal tubing circuit of FIG. 2 coupled with a sensor of the present invention.

The cassette assembly 18 includes front molded plastic plate 50 and back molded plastic plate 52, as shown in FIG. 4. The front and back plates 50 and 52 are hot welded together to define rectangular cassette member 56 having integral fluid conduits.

The cassette assembly 18 further includes a number of outwardly extending tubes 60, 62, 64, 66, and 68 that interconnect various integral fluid conduits and tubing assemblies. The outwardly extending tubes 60, 62, 64, 66, and 68 may be interconnected wherein each loop is engaged with a pumping device, such as pumping assemblies 70, 72, 74, 76 and 78 shown in FIG. 3.

Also included within the cassette assembly 18 is a first pressure sensing station 82 included in a first integral fluid conduit 80, and a second pressure sensing station 84 included in a second integral fluid conduit 86. As shown in FIG. 2, the first and second pressure sensing stations 82 and 84 of cassette assembly 18 each include a circular diaphragm 130 and 132.

A sensor 100, as shown in FIG. 4, can be mounted in the first and/or second pressure sensing stations 82 and 84 through openings 92 and 94 of cassette mounting plate 30 (shown in FIG. 3) via a snap-fit engagement. When the cassette assembly 18 is mounted to the cassette mounting plate 30, the sensor 100 protrudes through either opening 92 or opening 94 in cassette mounting plate 30. In this embodiment, the cassette mounting plate 30 and the front panel 110 may have two sensors (similar to sensor 100 in FIG. 4) that are mounted to protrude through openings 92 and 94. It should be appreciated that the cassette mounting plate 30 and the cassette assembly 18 may also be varied to provide sufficient structure to engage additional sensors.

The following description of the sensor 100, cassette assembly 18, cassette mounting plate 30 and front panel 110 will describe pressure sensing station 82. It should be appreciated that, in this embodiment, pressure sensing station 84 may have a structure similar to the description herewith to support a sensor similar to the sensor presented in FIG. 4.

As shown in FIG. 4, the circular diaphragm 130 is positioned on a raised cylindrical seat 134 on the back plate 52 of the cassette assembly 18. A ring-shaped plastic diaphragm retainer 118 is ultrasonic welded to the bottom surface 52 of cassette member 56 to establish a seal therebetween. This arrangement allows the diaphragm 130 to become mounted in a wall of the first integral fluid conduit 80 having a top wall 254 within the cassette assembly 18. The diaphragm 130 is, therefore, in direct fluid communication with the fluid in the first integral fluid conduit 80 and thus, this arrangement allows the diaphragm 130 to be directly responsive to fluid pressures within the first integral fluid conduit 80. It should be appreciated that since the first integral blood conduit 80 is in direct fluid communication with the blood removal tubing 22 and blood return tubing 24 which are fluidly connected via the common manifold 34, the first pressure sensing station 82 will be responsive to and the sensor 100 will sense the substantially common pressure or force exerted in both the blood removal tubing 22 and the blood return tubing 24 during operation.

Further, the diaphragm 130 is typically comprised of a flexible elastomeric material which can include, for example, a material selected from the group consisting of silicon compound elastomers and thermoplastic elastomers. In addition, the diaphragm 130 can be made from any material that adequately flexes to transmit force (i.e., allows force to be directly transmitted from one side of the material to the other without absorbing the force).

With further regard to the first pressure sensing station 82, FIG. 4 illustrates a direct coupling arrangement. This arrangement allows for the sensing of positive and negative pressures without a captive air space. To achieve the direct coupling, a ferromagnetic disk 122 is fixedly attached to a first surface of the diaphragm 130 that is not in direct contact with fluid in the first integral fluid conduit 80.

In this embodiment, the ferromagnetic disk 122 is bonded to the diaphragm 130 using an elastomeric connector piece 140. In another aspect of this embodiment, the ferromagnetic disk 122 may be directly bonded to the diaphragm 130 using an adhesive, such as a silicon based adhesive.

Figure 5:
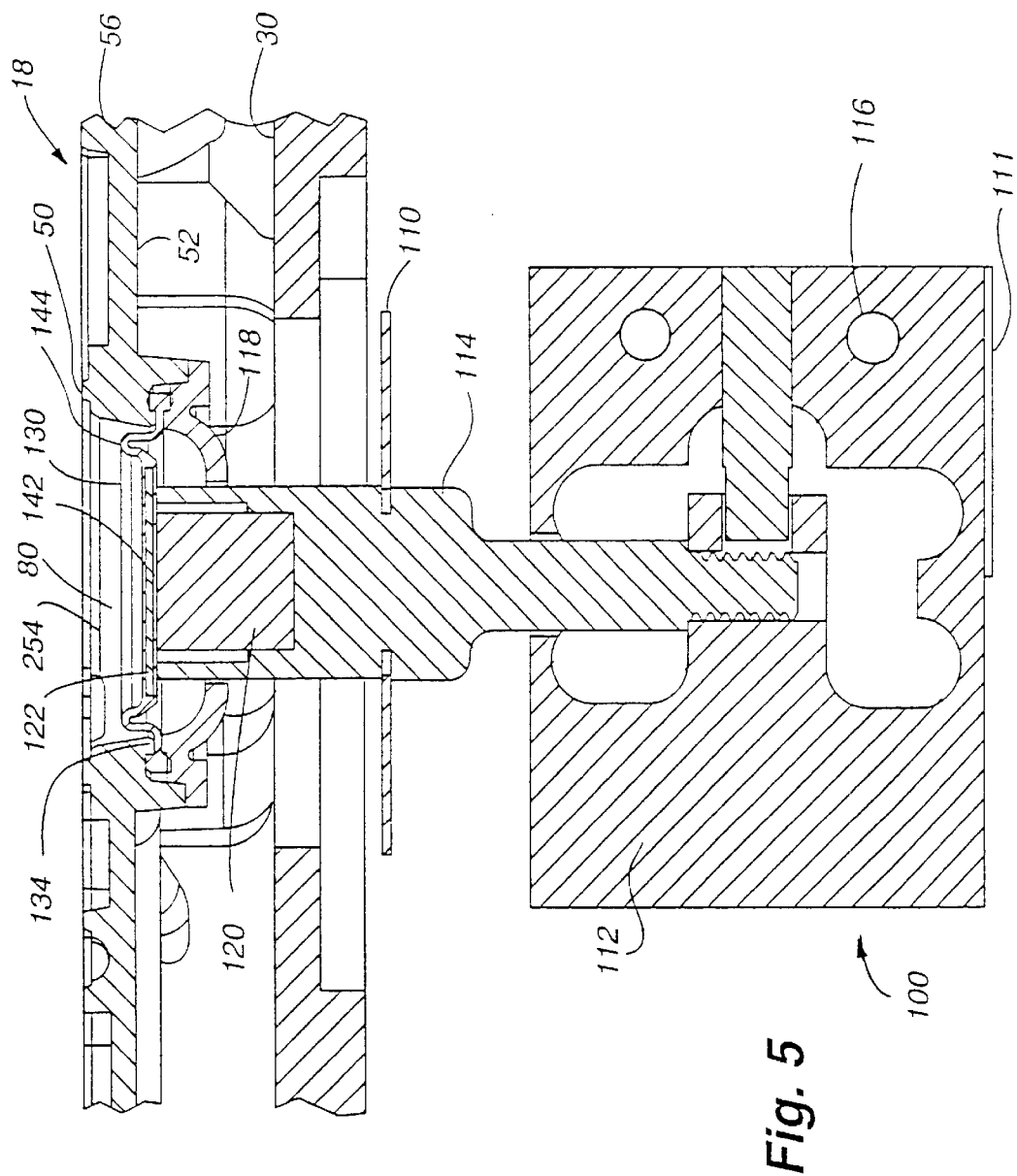
FIG. 5 is a cross-sectional view of a second embodiment of a pressure sensing module of the extracorporeal tubing circuit of FIG. 2 coupled with a sensor of the present invention.

In yet another aspect of embodiment, as shown in FIG. 5, the ferromagnetic disk 122 may be injection molded within the diaphragm 130. At the surface where the ferromagnetic disk 122 is connected to the magnet 120, a circular exposed area 142 is created by a pin holding the insert that exposes the metal surface of the ferromagnetic disk 122. In one embodiment, the circular exposed area 142 has a diameter of about 0.25 inches.

The ferromagnetic disk 122 allows the surface of the diaphragm 130 to be removably attached to the sensor 100. In this manner, the cassette assembly 18, which includes the diaphragm 130 and other components which come into direct contact with blood, can be readily detached from reusable components and disposed of after a single use. The reusable components of the extracorporeal blood processing system, such as support structures, pumps and so on, are not disposable and can then be used with a subsequent disposable assembly for a subsequent patient after use with a first patient. Thus, it will be appreciated that the disposable 10 does not include the sensor 100 but is removably attachable thereto.

In removably coupling the sensor 100 to the cassette assembly 18, the sensor 100 includes a magnet 120. In this instance, the magnet 120 and the ferromagnetic disk 122 can be directly coupled by bringing them into close enough proximity to each other. It should be appreciated that the reverse arrangement may be accomplished wherein a magnet may be fixedly attached to the diaphragm 130 and a ferromagnetic disk may be connected to the sensor 100.

A first end of a magnet holder 114 supports and places the magnet 120 in contact with ferromagnetic disk 122. The magnet holder 114 is integrally mounted with the cassette mounting plate 30 and the front panel 110. A second end of the magnet holder 114 is mounted to a load cell 112 that is also connected to the front panel 110 via mounting bracket 116. The load cell 112 includes a transducer 111 which, in this embodiment, is attached to an outer portion of the load cell 112.

To assist in detachment of the magnet 120 from the ferromagnetic disk 122, a retainer 118 is provided. The retainer 118 structurally limits the travel of the diaphragm 130. As the magnet 120 is moved for detachment, the diaphragm 130 and the ferromagnetic disk 122 make contact with the retainer 118. At this point of contact, the force used to move the diaphragm 130 will be transferred to the retainer 118 allowing the diaphragm 130 to be removed from the magnet 120 without undue flexure that could cause damage. It should be appreciated that this detachment mechanism can be included in all embodiments described in the present invention.

To further assist in detachment and attachment of the sensor 100 from the ferromagnetic disk 122, the diaphragm 130 may have one or more convolute portions 144 that allow the ferromagnetic disk 122 to easily couple with the magnet 120. Such convolute portions 144 are non-planar portions of the diaphragm surface which allows for an increased range of motion of the diaphragm 130 so that the diaphragm 130 can be readily attached to the sensor 100. The convolute portions 144 allow the diaphragm 130 to flex when the cassette assembly 18 is mounted to the cassette mounting plate 30. This flexure of the diaphragm 130 enables the ferromagnetic disk 122 to engage with the magnet 120 within the tolerance limits of the transducer 111 such that the transducer 111 may not need to be electronically set to zero every time a cassette assembly 18 is loaded.

As such, the convolute portions 144 have the advantage that they may enable pressure measuring hardware and software to be created without adding additional systems that provide for zeroing the transducer 111. In addition, the convolute portions 144 allow for another significant advantage in the present invention. By use of the convolute portions 144, as discussed above, an increased range of motion of the diaphragm 130 is achieved. This increased range of motion can be attained even with a diaphragm which is sufficiently thick to avoid significant concerns regarding pinholes and leaks. Such concerns are particularly important in extracorporeal blood processing systems where health and safety concerns are present. More particularly, in a preferred embodiment, the diaphragm 130 has a thickness of greater than about 0.001 inches, more preferably greater than about 0.010 inches and most preferably about 0.020 inches. Further, it should be recognized that the thickness of the diaphragm can be significantly greater, as well.

In the structure of the present invention, fluid pressure in the first integral fluid conduit 80 is transferred from the diaphragm 130 to the magnet 120 via the ferromagnetic disk 122. The magnet 120 transfers the force via the magnet holder 114 to the load cell 112 and the transducer 111. The load cell 112 is, typically, composed of a resilient material, such as aluminum, and formed as a spring. In FIG. 4, the load cell 112 is shaped in the form of a double beam. This shape tends to reduce twisting or torsion of the load cell 112 so that forces applied to the load cell 112 are linearly conveyed throughout the structure. The transducer 111 is attached to the load cell 112 and senses the forces or distortion of the load cell 112. When composed of aluminum, the load cell 112 may obtain deflections ranging from about 0.002 to 0.02 inches.

In one aspect of this embodiment, a transducer 111, such as a strain gauge, is capable of directly measuring a force exerted on the diaphragm 130 by the fluid pressure in the first integral fluid conduit 80. The transducer 111 converts the force exerted on the diaphragm 111 to an electrical signal. As such, positive and negative pressures exerted on the diaphragm 130 may be measured in the form of stresses or strains. By correlating the force measurement to the area on which the force is acting, the pressure exerted on the diaphragm 111 can be calculated.

In another aspect of this embodiment, a transducer 111, such as a piezoelectric distance sensor or a linear variable differential transformer (LVDT), is capable of measuring displacement of the diaphragm 130. The displacement measurement is capable of being correlated into a positive or negative pressure depending on the direction of displacement of the diaphragm 130 and the spring rate of the diaphragm 130.

Figure 6:
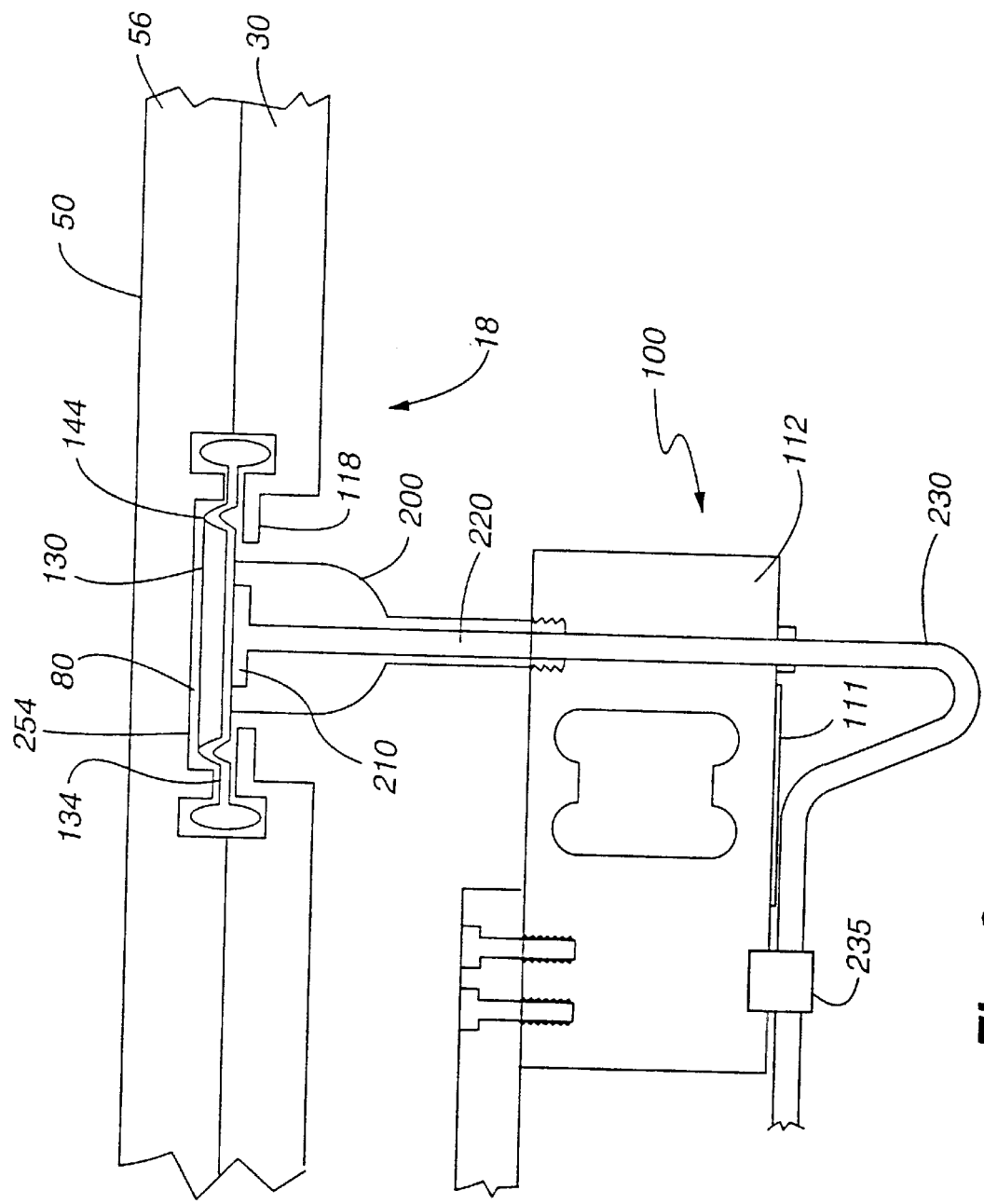
FIG. 6 is a cross-sectional view of a third embodiment of a pressure sensing module of the extracorporeal tubing circuit of FIG. 2 coupled with a sensor of the present invention.

Another embodiment of sensor 100 is shown in FIG. 6. In this embodiment, the sensor 100 may be directly coupled to the diaphragm 130 using vacuum pressure. The sensor 100 includes a probe 200 that is connected to the load cell 112. The probe 200 includes a vacuum chamber 210 that is connected to a vacuum line 220 which passes through the probe 200 and the load cell 112. A flexible vacuum hose 230 connects the vacuum line 220 to a vacuum source, not shown. The vacuum source may include a device that is capable of creating a vacuum pressure, such as a vacuum pump.

An anchor support 235 may be used to secure the vacuum hose 230 so that flexing of the hose 230 does not unduly influence the sensor 100 readings. The vacuum hose 230 may optionally be coiled. In this configuration, the forces applied to the hose 230 will have a reduced effect on the readings of sensor 100. In addition, the vacuum hose 230 may be held by other means know to those skilled in the art for reducing the influences that the vacuum hose 230 has on the readings of sensor 100.

In this embodiment, as shown in FIG. 6, the top wall 254 of conduit 80 assists in coupling the sensor 100 to the diaphragm 130. As the sensor 100 is moved toward the diaphragm 130 for coupling, the top wall 254 is positioned to make contact with the diaphragm 130. This contact with the top wall 254 prevents undue flexure of the diaphragm 130. After coupling between the diaphragm 130 and the sensor 100 is established, the sensor 100 is moved such that the diaphragm 130 is backed off from contact with the top wall 254. This technique can be used to assist coupling in other embodiments, including that shown in FIG. 7.

In operation, a vacuum coupling is created when the vacuum chamber 210 interfaces with the diaphragm 130 while the vacuum source creates a vacuum pressure in the vacuum hose 230, vacuum line 220 and vacuum chamber 210. When a vacuum pressure is created, the diaphragm 130 is coupled to the vacuum chamber 210. This coupling allows the sensor 100 to measure the force exerted on or the displacement of the diaphragm 130 by fluid in the fluid conduit 80 similar to the magnetic coupling previously discussed.

In addition, this embodiment allows the state of coupling between the diaphragm 130 and the sensor 100 to be determined and monitored. The determination of proper coupling is achieved by using a device that is capable of monitoring the vacuum pressure or air flow in the vacuum hose 230, line 220 and chamber 210. If vacuum pressure is lost or air flow is detected, the sensor 100 is not coupled to the diaphragm 130. Conversely, if vacuum pressure is sensed or air flow is not detected, the sensor 10 is properly coupled to the diaphragm 130. It can be critically important to monitor the coupling of the sensor 100 or probe 200 with the diaphragm 130 because improper coupling could cause erroneous pressure measurement that could have drastic effects on a patient/donor.

Figure 7:
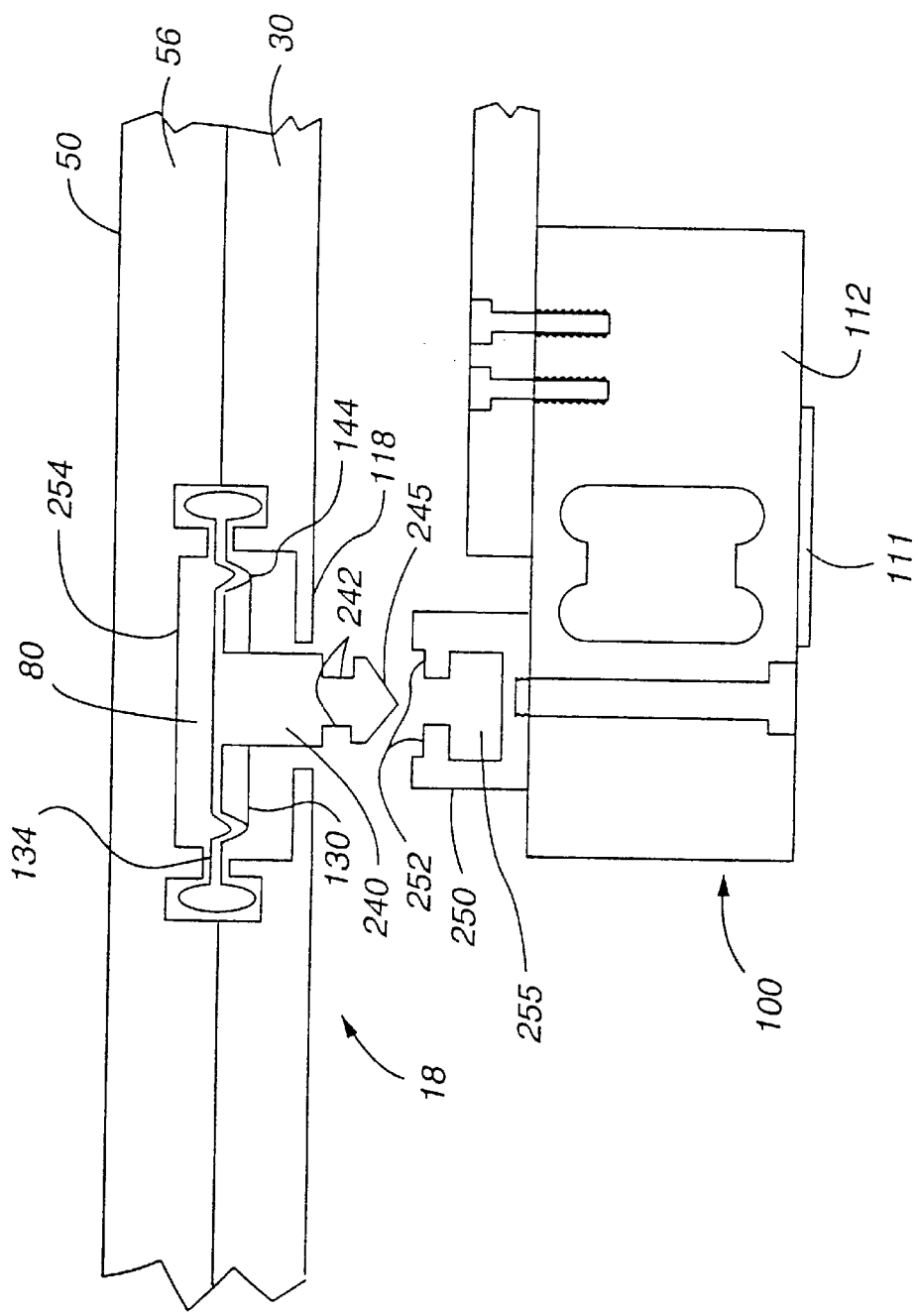
FIG. 7 is a cross-sectional view of a fourth embodiment of a pressure sensing module of the extracorporeal tubing circuit of FIG. 2 and a sensor of the present invention.

In yet another embodiment of the present invention, as shown in FIG. 7, the sensor 100 may be coupled to the diaphragm 130 using a receiving structure 250 which is connected to the load cell 112. In this embodiment, the diaphragm 130 includes an elongated portion 240 connected to a first side of the diaphragm 130 that is not in fluid communication with the fluid in fluid conduit 80. The elongated portion 240 terminates in a shaped end 245. The shaped end 245 may have many configurations, such as a rounded, pointed or spiral/screw end piece.

It should be noted that the elongated member 240 may be integrally molded with the diaphragm 130 or may be affixed to the diaphragm 130 by an adhesive material. Also, the elongated member 240 and shaped end 245 may be composed of a resilient material, such as an elastomer, to allow the shaped end 245 to be inserted in the receiving structure 250. In addition, in one aspect, the elongated member 240 may be cylindrical in shape and the cut-out segments 242 may be located annularly around the cylindrical elongated member 240. In this aspect, the receiving structure may comprise a circular opening into which the cylindrical shaped end 245 can be inserted.

In this embodiment, the sensor 100 is moved vertically toward the cassette assembly 18 via any appropriate means, such as a servo motor. As the sensor 100 moves, the shaped end 245 engages the receiving structure 250 at shoulders 252. Further movement of the sensor 100 causes the shaped end 245 to be pushed between the shoulders 252 into interior portion 255 of the receiving structure 250. A top wall 254 of the fluid conduit 80 is positioned to allow the diaphragm 130 to touch the top wall 254 during coupling. The contact of the diaphragm 130 with the top wall 254 allows the diaphragm 130 to be positioned in and coupled with the receiving structure 250 without placing undue stresses on or causing extreme flexure of the diaphragm 130. After the diaphragm 130 is coupled to the receiving structure 250, the sensor 100 is moved by the servo motor, not shown, such that the diaphragm 130 is backed off from contact with the top wall 254.

The movement of the sensor 100 is stopped when the shoulders 252 of the receiving structure 250 engage the cut-out segments 242 of the elongated portion 240. Once the cut-out segments 242 engage the shoulders 252, the diaphragm 130 is coupled with the receiving structure 250. The sensor 100 can be further moved such that the diaphragm 130 is positioned away from wall 254 to a neutral position (as shown in FIG. 7 which illustrates an uncoupled configuration). This position allows the diaphragm 130 to flex normally inward in response to a negative fluid pressure in fluid conduit 80. During detachment, retainer 118 is provided to structurally limit the travel of the diaphragm 130. As the cassette assembly 18 is moved for detachment, the diaphragm 130 makes contact with the retainer 118. At this point of contact, the forces used to move the diaphragm 130 are transferred to the retainer 118. Thus, the diaphragm 130 is detached from the receiving structure 250 without being subjected to undue flexure that could cause damage.

In another aspect of this embodiment, the receiving structure 250 may comprise a slotted opening that allows the shoulder portions 252 to be horizontally advanced such that the cut out segments 242 of the diaphragm 130 engage the shoulder portions 252. In this aspect, the receiving structure 250 can engage the elongated portion 240 without causing undue flexure of the diaphragm 130.

In yet another aspect of this embodiment, the shaped end 245 may comprise a spiral or screw type shape. In this aspect, the receiving structure 250 includes a complementary spiral or screw threaded opening. Therefore, the receiving structure 250 engages the shaped end 245 by having either the cassette member 18 or the sensor 100 rotate such that the two structures are threadily engaged.

Figure 8:
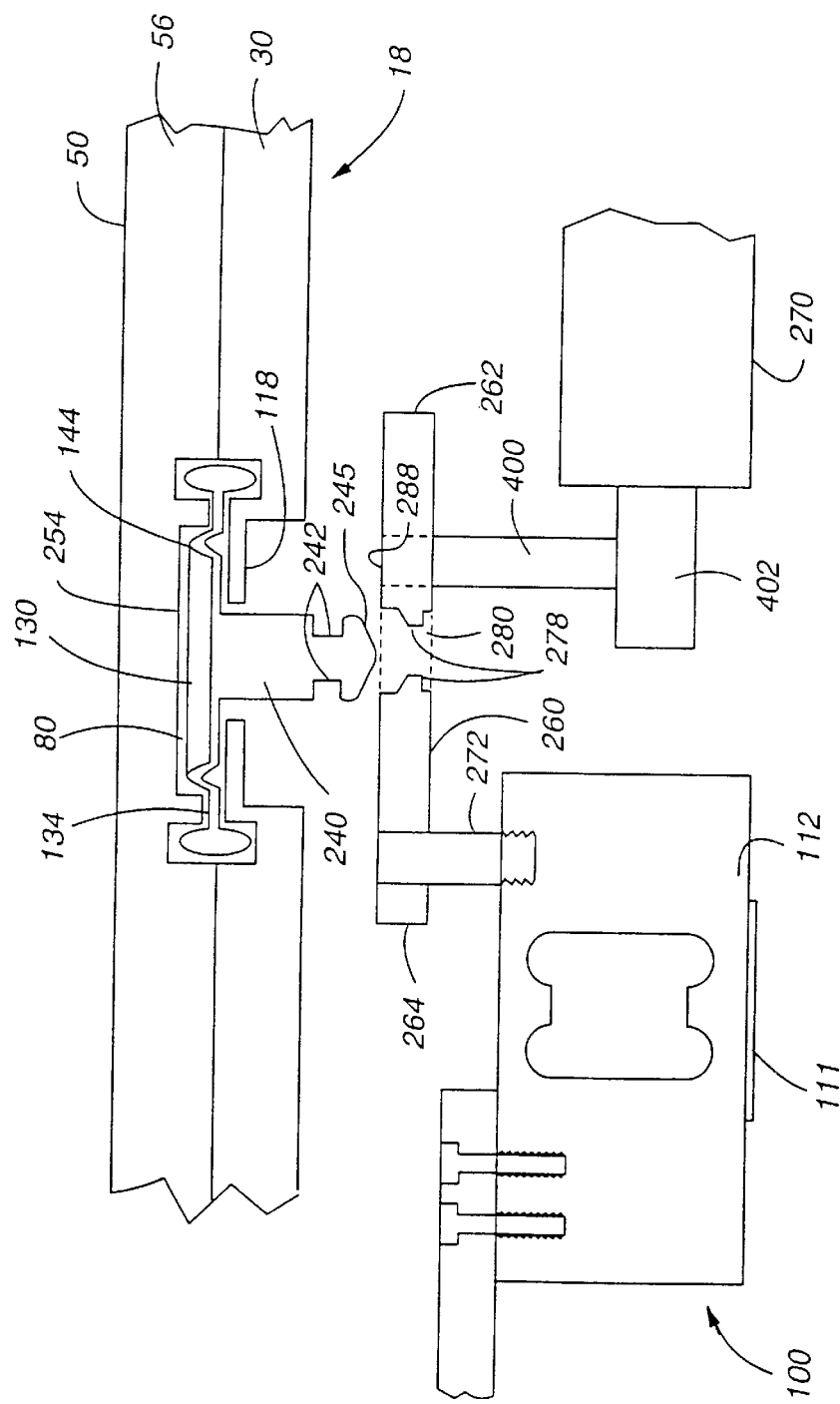
FIG. 8 is a cross-sectional view of a fifth embodiment of a pressure sensing module of the extracorporeal tubing circuit of FIG. 2 and a sensor of the present invention.

In even another embodiment of the present invention, the sensor 100, as shown in FIG. 8, may be directly coupled using a receiving element 260. In this embodiment, the diaphragm 130 includes an elongated portion 240 extending from a first side of the diaphragm 130 that is not in fluid communication with the fluid in the fluid conduit 80.

The elongated portion 240 terminates in a shaped end 245 having cut-out segments 242. In one aspect, the elongated portion 240 and the shaped end 245 are integrally molded as part of the diaphragm 130. In another aspect, the elongated portion 240 may be secured to the diaphragm 130 using, for example, an adhesive. The elongated portion 240 and shaped end 245 may be composed of a resilient matter, such as an elastomeric material.

The receiving element 260 is adapted to capture the shaped end 245 of the elongated portion 240 and, thus, couple the diaphragm 130 with the load cell 112 of the sensor 100. Specifically, the receiving element 260 is fixedly attached at a first end 264 via support structure 272 to the load cell. The receiving element 260 includes an opening 280 that has shoulder portions 278 capable of engaging cut-out segments 242 of the elongated portion 240. A post 400 is connected to a plunger 402 of solenoid 270. The post 400 is positioned in slot 288 located in a second end 22 of the receiving element 260. The solenoid 270, through post 400, moves to open the receiving element 260 to capture the shaped end 245. When the solenoid is then deenergized, a spring (not shown) returns plunger 402 to its initial position allowing the spring in receiving element 260 to close the receiving element 260, gripping shaped end 245.

It should be appreciated that, when opening 280 captures shaped end 245, the receiving element 260 may have means for detecting a state of attachment. The attachment may be monitored by use of mechanical switches, proximity sensors, or other devices known to one skilled in the art for detecting a state of attachment or coupling.

In addition, it should also be appreciated that during coupling of the sensor 100 with the elongated portion 240, the opening 280 may not perfectly align with the shaped end 245. In these instances, top wall 254 is provided to physically limit the travel of the diaphragm 130. As such when a misalignment occurs and forces are exerted on the diaphragm 130 during coupling, the diaphragm 130 will not be subjected to undue flexure that could cause damage. It should also be noted that when coupling of the diaphragm 130 with the receiving element 260 is made with the diaphragm flexed against the top wall, the sensor 100 must be moved such that the diaphragm 130 is backed off from contact with the top wall 254 for proper operation.

Additionally, in the instances of misalignment during decoupling, retainer 118 is provided to limit the travel of the diaphragm 130. In these instances, the retainer 118 prevents the diaphragm 130 from experiencing undue flexure when forces are exerted on the diaphragm 130 during decoupling.

Figure 9:
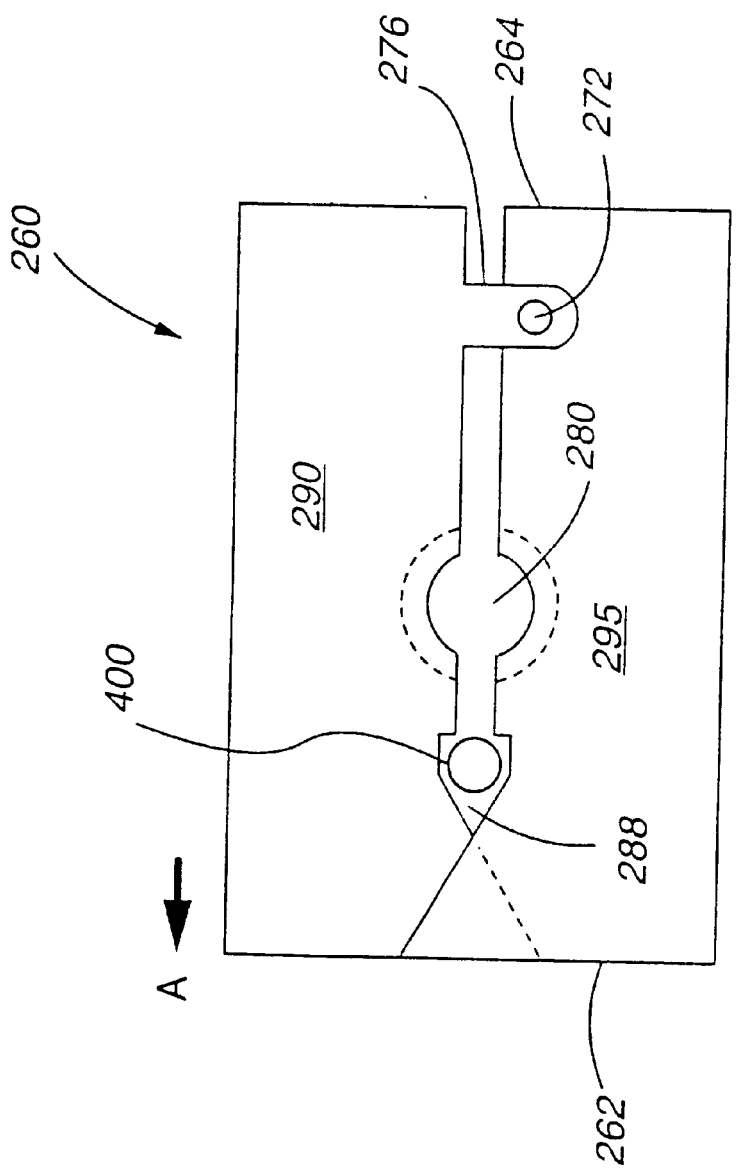
FIG. 9 is a top view of one embodiment of the receiving element of the fifth embodiment of the pressure sensing module.

In one aspect of this embodiment, the receiving element 260, shown in FIG. 9, includes a first section 290 and a second section 295 connected by hinge 276. The post 272 is included in the hinge 276 which is spring loaded to induce the receiving element 260 in a closed orientation. In another aspect, the first section 290 and second section 295 may optionally overlap at second end 262. Additionally, the post 400 extends through the receiving element 260 via slot 288.

In operation, the solenoid 270, as shown in FIG. 8, moves in the direction of arrow A, as shown in FIG. 9. As such, the plunger 402 causes the post to move within slot 288 and impinge on the overlapping areas of first and second sections 290 and 295 causing the receiving element 260 to open. As the receiving element 260 opens, the first and second portion 290 and 295 hinge away from each other at the second end 262 causing the opening 280 to become larger.

Once the hinging of the receiving element 260 induces the opening 280 to be large enough to accept the shaped end 245 of the elongated portion 240, the cassette member 18 is moved vertically toward the sensor 100 such that the shaped end 245 is inserted into opening 280.

Once the shaped end 245 has entered opening 280, the solenoid 270 directs the plunger 402 to move in the opposite direction of arrow A, shown in FIG. 9. This movement allows the spring-loaded hinge 276 to induce the first and second portions 290 and 295 toward each other, thus, reducing the size of opening 280. This hinging action stops when the post 400 is free in slot 288. At this position, post 400 should not impinge on the sides of the slot 288.

Additionally, as the first and second sections 290 and 295 hinge together the opening 280 becomes smaller to close around the shaped end 245 of the elongated portion 240 such that the shoulder portions 278 are engaged into the cut-out segments 242 of the elongated portion 240. Thus, the shaped end 245 is captured in the receiving element 260 coupling the diaphragm 130 with the sensor 100.

Figure 10:
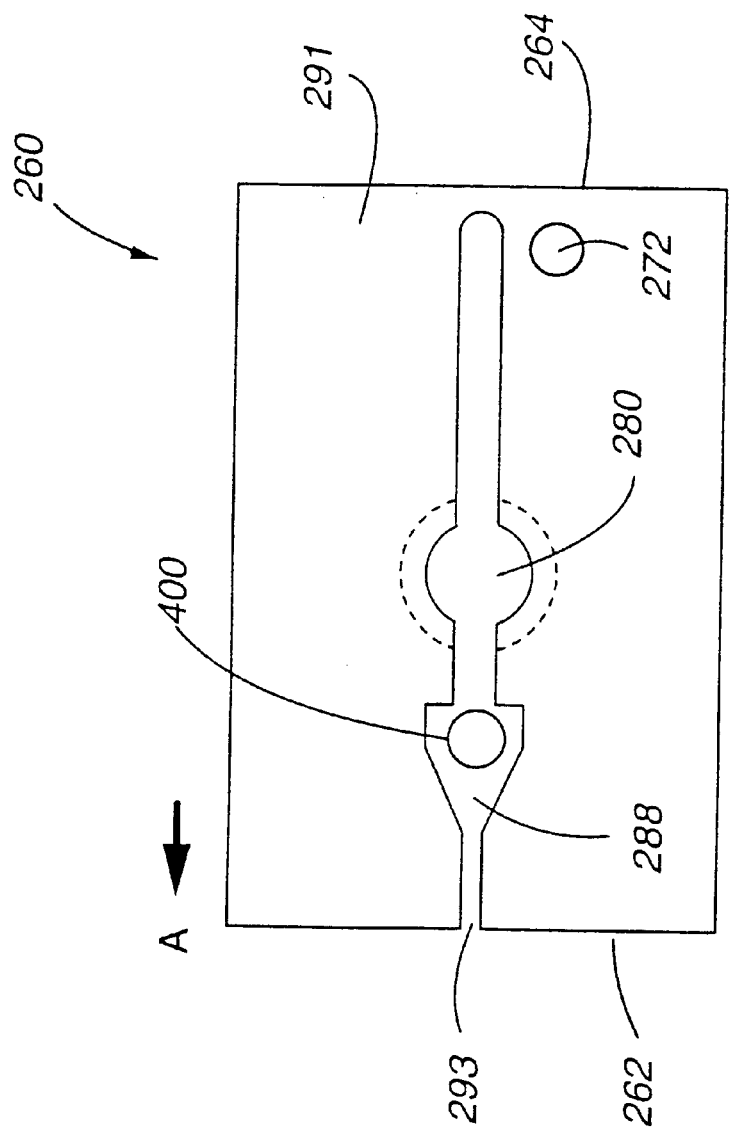
FIG. 10 is a top view of another embodiment of the receiving element of the fifth embodiment of the pressure sensing module.

In another aspect of this embodiment, as shown in FIG. 10, the receiving element 260 includes a single section 291. The single section 291 is closed at a first end 264 and has a gap 293 at a second end 262. The post 400 extends through the receiving element 260 via slot 288.

The single section 291 may be composed of an elastomeric material or, more preferably, a metallic element designed to allow flexure within its elastic or spring range. The width of gap 293 is smaller than the width of the post 400 such that when the post 272 is moved in the direction of arrow A and into gap 293, the receiving element 260 flexes open.

This flexure caused by post 400 allows the opening 280 to become larger to accept the shaped end 245 of the elongated portion 240, shown in FIG. 8. As explained previously, once the opening 280 is large enough to accept the shaped end 245, the cassette member 18 is vertically moved toward the sensor 100, and the shaped end 245 is inserted into opening 280. As the shaped end 245 enters the opening 280, the post 400 may then be moved in the opposite direction of arrow A and retracted from gap 293. This retraction causes opening 280 to become smaller and close around shaped end 245. At this point, shoulder portions 228 engage cut-out segments 242 to capture the shaped end 245.

The foregoing description of the present invention has been presented for the purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiment described herein above and further intended to explain best modes known of practicing the invention and to enable others skilled in the art to utilize the invention is such, or other embodiments and with various modifications required by the particular application(s) or use(s) of the present invention. It is intended that the appended claims be construed to include alternative embodiments to the extent permitted by the prior art.

What is claimed is:

1. An extracorporeal blood processing system in which blood is removed from an individual for processing and returned to the individual, said system comprising:
   a blood removal conduit for transferring blood from a donor/patient;
   a blood return conduit for transferring blood to a donor/patient;
   said blood removal conduit and said blood return conduit being in fluid communication; and
   a disposable assembly including a pressure sensing station and a plurality of integral passageways for transporting blood, each of said plurality of integral passageways being partially defined by at least one of said blood removal conduit and said blood return conduit;

said pressure sensing station including a diaphragm member mounted to said disposable assembly, said diaphragm member having a first surface being in direct fluid communication with one of at least said blood removal conduit and said blood return conduit, said diaphragm member being movably responsive in relation to the fluid pressure commonly occurring within each of such blood removal and blood return conduits;

a sensor for determining a pressure in one of at least said blood removal conduit and said blood return conduit; and means for removably attaching a second surface of said diaphragm to said sensor wherein said pressure sensing station co-acts with said sensor to measure the fluid pressure commonly occurring within each of said blood removal and blood return conduits.

2. An extracorporeal system, as claimed in claim 1, wherein said sensor includes a force sensor for measuring a force exerted by fluid on said first surface of said diaphragm member, said force corresponding to a pressure of fluid in at least one of said blood removal conduit and said blood return conduit.

3. An extracorporeal system, as claimed in claim 1, wherein said disposable assembly comprises a molded cassette member.

4. An extracorporeal system, as claimed in claim 1, wherein said diaphragm member comprises a flexible elastomeric material.

5. An extracorporeal system, as claimed in claim 1, wherein said means for removably attaching further comprises:

a ferromagnetic material attached to said second surface of said diaphragm member; and a magnet attached to said sensor for coupling to said ferromagnetic material.

6. An extracorporeal system, as claimed in claim 1, wherein said means for removably attaching further comprises:

a magnet attached to said second surface of said diaphragm member; and a ferromagnetic material attached to said sensor for coupling to said magnet.

7. An extracorporeal system, as claimed in claim 1, wherein said sensor includes a strain gauge.

8. An extracorporeal system, as claimed in claim 1, wherein said sensor measures positive and negative pressures in said at least one of said blood removal conduit and said blood return conduit.

9. An extracorporeal system, as claimed in claim 1, wherein said sensor measures a pressure of blood being removed from said donor/patient and a pressure of blood being returned to said donor/patient.

10. An extracorporeal system, as claimed in claim 1, wherein said extracorporeal blood processing system is an apheresis system.

11. An extracorporeal blood processing system, as claimed in claim 1, wherein said means for removably attaching further comprises:

a probe having a vacuum chamber for interfacing with said second surface of said diaphragm member, said probe being interconnected to said sensor, wherein a vacuum created in said vacuum chamber couples said probe to said second surface of said diaphragm member.

12. A disposable assembly, as claimed in claim 1, further comprising means for detecting a state of coupling between said vacuum chamber and said second surface of said diaphragm member.

13. An extracorporeal blood processing system, as claimed in claim 1, wherein:

said diaphragm member further comprising:

an elongated member attached to and extending from said second surface of said diaphragm member; and said means for attaching further comprising:

means for capturing connected to said sensor, said means for capturing engaging said elongated member.

14. An extracorporeal blood processing system, as claimed in claim 1, wherein said diaphragm member further comprises:

an elongated member attached to and extending from said second surface of said diaphragm member, said elongated member having a shaped end; and said means for attaching further comprising:

a receiving element having a first opening, said first opening having a first size for inserting said shaped end into said receiving element and said opening having a second size for capturing said shaped end in said receiving element, said first size being larger than said second size.

15. An extracorporeal blood processing system, as claimed in claim 14, wherein said means for attaching further comprises:

said receiving element having surfaces defining a second opening;

a cam positioned within said second opening; and a solenoid attachable to said cam, wherein said solenoid moves said cam against said surfaces defining a second opening to cause said first opening to expand and contract from said first size to said second size.

16. An extracorporeal blood processing system as claimed in claim 14, wherein said receiving element further comprises:

a first body piece;

a second body piece, said first and second body pieces defining said opening; and a hinge element connecting said first and second body pieces, wherein said hinge element causes said first opening to expand and contract from said first size to said second size.

17. An extracorporeal blood processing system as claimed in claim 14, wherein said receiving element further comprises:

a single section being closed at a first end and having a gap at a second end, said gap further defining said first opening;

said gap being expanded and contracted within the elastic range of said single section causing said first opening to expand and contract from said first size to said second size.

18. An extracorporeal blood processing system, as claimed in claim 1, wherein:

said diaphragm member further comprises:

an elongated member attached to said second surface of said diaphragm member, said elongated member includes a shaped end; and said means for attaching further comprising:

a receiving structure having a opening, said opening having a complementary shape corresponding with said shaped end, wherein said opening captures said shaped end.

19. A disposable assembly, as claimed in claim 1, further comprising:

a single needle, in direct fluid communication with said blood removal conduit and blood return conduit, for removal of blood from and return of blood to said donor/patient.

20. A method for measuring pressure in an extracorporeal blood processing system, comprising the steps of:

introducing blood from a donor/patient into a disposable assembly having at least one blood conduit, said at least one blood conduit having a diaphragm member disposed within a wall of said at least one blood conduit; and determining a pressure in said at least one blood conduit comprising measuring a force of said blood on said diaphragm using a sensor comprising measuring strain exerted on said diaphragm by said blood by using a strain gauge; and measuring stress exerted on said diaphragm by said blood by using a strain gauge; and calculating a pressure of said blood in said at least one blood conduit using the force exerted on said diaphragm member obtained from said measuring step.

21. The method, as claimed in claim 20, wherein said sensor is removably coupled to said diaphragm member.

* * * * *

UNITED STATES PATENT AND TRADEMARK OFFICE
CERTIFICATE OF CORRECTION

PATENT NO. : 6,764,460 B2  Page 1 of 1
APPLICATION NO. : 09/911955
DATED : July 20, 2004
INVENTOR(S) : Victor D. Dolecek, John J. Kappus and Mark Joseph Brierton It is certified that error appears in the above-identified patent and that said Letters Patent is hereby corrected as shown below:

Column 14, line 1, claim 12 - "as claimed in claim 1" should be "as claimed in claim 11"

Signed and Sealed this

Twenty-fifth Day of July, 2006

JON W. DUDAS
*Director of the United States Patent and Trademark Office*